(12) United States Patent
Kim et al.

(10) Patent No.: US 10,155,007 B2
(45) Date of Patent: Dec. 18, 2018

(54) SYNTHESIS METHOD FOR IMPROVED TENOFOVIR DISOPROXIL FUMARATE USING ION-EXCHANGE RESIN AND METHOD FOR PREPARING ORAL DISSOLVING FILM FORM USING THE SAME

(71) Applicant: Firson, Seobuk-gu, Cheonan-si (KR)

(72) Inventors: Dong-Jin Kim, Seoul (KR); Chang-Hui Koo, Ansan-si (KR); Il-Hee Cho, Bucheon-si (KR); Sung-Bae Lee, Yangju-si (KR); Dong-Hoon Han, Seoul (KR)

(73) Assignee: FIRSON (KR)

( * ) Notice: Subject to any disclaimer, the term of this patent is extended or adjusted under 35 U.S.C. 154(b) by 0 days.

(21) Appl. No.: 15/521,164

(22) PCT Filed: May 19, 2015

(86) PCT No.: PCT/KR2015/004949
§ 371 (c)(1),
(2) Date: Apr. 21, 2017

(87) PCT Pub. No.: WO2016/068430
PCT Pub. Date: May 6, 2016

(65) Prior Publication Data
US 2017/0354668 A1     Dec. 14, 2017

(30) Foreign Application Priority Data

Oct. 29, 2014 (KR) .................... 10-2014-0148265

(51) Int. Cl.
| | | |
|---|---|---|
| A61K 31/6615 | (2006.01) | |
| C07F 9/6561 | (2006.01) | |
| A61K 31/52 | (2006.01) | |
| C07F 9/09 | (2006.01) | |
| A61K 31/683 | (2006.01) | |
| A61K 9/00 | (2006.01) | |
| A61K 9/70 | (2006.01) | |
| A61K 47/12 | (2006.01) | |
| C07C 57/15 | (2006.01) | |

(52) U.S. Cl.
CPC ........ *A61K 31/6615* (2013.01); *A61K 9/0056* (2013.01); *A61K 9/7007* (2013.01); *A61K 31/52* (2013.01); *A61K 31/683* (2013.01); *C07F 9/09* (2013.01); *C07F 9/65616* (2013.01); *A61K 47/12* (2013.01); *C07C 57/15* (2013.01)

(58) Field of Classification Search
None
See application file for complete search history.

(56) References Cited

U.S. PATENT DOCUMENTS

| | | |
|---|---|---|
| 2013/0165413 A1 | 6/2013 | Chava et al. |
| 2014/0303368 A1 | 10/2014 | Indukuri et al. |

FOREIGN PATENT DOCUMENTS

| | | | | |
|---|---|---|---|---|
| CN | 1634943 A | | 7/2005 | |
| CN | 101948485 A | * | 1/2011 | ........... A61K 31/675 |
| CN | 101948485 A | | 1/2011 | |
| CN | 101239189 B | | 6/2011 | |
| CN | 102219805 A | | 10/2011 | |
| CN | 102295660 A | | 12/2011 | |
| CN | 103374039 A | | 10/2013 | |
| CN | 102899367 B | | 4/2014 | |
| CN | 103848868 A | | 6/2014 | |

OTHER PUBLICATIONS

Liew, Kai. AAPS PharmSciTech 13(1) (2012) 134-142.*
Lisa M. Schultze et al., Practical Synthesis of the anti-HIV Drug, PMPA, Tetrahedron Letters, Tetrahedron Letters 39 (1998) 1853-1856, Process Chemistry and Analytical Chemistry, Gilead Sciences, 353 Lakeside Drive, Foster City, CA 94404.
David H. Brown Ripin et al., Process Improvements for the Manufacture of Tenofovir Disoproxil Fumarate at Commercial Scale, Organic Process Research & Development 2010, 14, 1194-1201, vol. 14 No. 5, 2010.
L. Santos, Tenofovir Disoproxil Fumarate, Authorized USP Pending Monograph, Version 1, (2011).
Tenofovir Tablets: Final text for addition to The International Pharmacopoeia, World Health Organization, Jun. 2010.

* cited by examiner

*Primary Examiner* — Deepak R Rao
*Assistant Examiner* — Laura M Daniel
(74) *Attorney, Agent, or Firm* — David R. Stevens; Stevens Law Group

(57) ABSTRACT

The present invention relates to a synthesis method of preventing the formation of impurities and byproducts in the synthesis of tenofovir disoproxil fumarate (Teno-DF) used as a medicine for hepatitis B and HIV treatment due to its function to promote bioactivities. In the synthesis method of the present invention, an ion-exchange resin (Dowex 50W hydrogen form, sulfonic acidic cation exchange resin) is used to enhance the yield and purity of the compound. The present invention also relates to a method of preparing an oral dissolving film dosage form in the manufacture of a medicine using the tenofovir compound with high purity obtained by the synthesis method of the present invention as an effective ingredient.

3 Claims, 13 Drawing Sheets

US 10,155,007 B2

SYNTHESIS METHOD FOR IMPROVED TENOFOVIR DISOPROXIL FUMARATE USING ION-EXCHANGE RESIN AND METHOD FOR PREPARING ORAL DISSOLVING FILM FORM USING THE SAME

TECHNICAL FIELD

The present invention relates to a method for effectively synthesizing a tenofovir and its derivatives used as a medicine for hepatitis B and AIDS due to their antiviral properties using a proper catalyst and an ion-exchange resin. The present invention also relates to a method for preparing a medicine for hepatitis B and HIV treatment using tenofovir disoproxil fumarate obtained with high purity through the synthesis method as an effective ingredient into an oral dissolving film as a drug dosage form.

There has never been a report on the synthesis of tenofovir disoproxil fumarate like the present invention. Particularly, the synthesis of tenofovir includes hydrolysis and alkali-involved neutralization subsequent to hydrolysis in the intermediate process. Thus, a lot of byproducts and degradation products are produced from the hydrolysis and neutralization processes and integrated into tenofovir, which is yielded as a final product. Yet, the tenofovir obtained together with the byproducts and degradation products is poor in solubility to water and produced at low yield because of its inclusion of crystal water, so it is necessary to eliminate the crystal water from the tenofovir molecules before the subsequent reaction step in order to reduce the yield of different ester compounds formed as byproducts. A conventional solution to this problem is a low-pressure drying process performed at high temperature to remove crystal water from the tenofovir $H_2O$ (MW 305.3). However, the synthesis method of the present invention eliminates the need of performing the low-pressure drying process at high temperature by minimizing the byproducts formed in the synthesis step of tenofovir. Also, the synthesis method of the present invention uses an ion-exchange resin to precisely neutralize the synthesis solution and treats the solution with an organic solvent to enable a simple low-pressure drying process at low temperature, ending up producing tenofovir disoproxil fumarate at high purity with minimized byproducts and degradation products.

The present invention also relates to a method for preparing an oral dissolving film as a drug dosage form for easiness of administration and fast action in biological activities in the preparation of a medicine for the treatment of hepatitis B and HIV using the tenofovir disoproxil fumarate of the synthesis method as an effective ingredient.

BACKGROUND ART

The principal ingredient of Viread® tablets, a medication developed by Gilead Sciences Inc. (U.S.A.) and used to treat hepatitis B, has a general name of tenofovir disoproxil fumarate (hereinafter, referred to as "Teno-DF"); its melting point (MP) is 219° C., its MW is 635.52 and its chemical name according to the structural formula is 9-[2-(R)-[[[bis[[(isopropoxycarbonyl)oxy]methoxy]phosphinyl]]methoxy] propy1] adenine fumarate.

The Teno-DF was approved by the U.S. FDA in 2001, for the treatment of HIV, and in 2008 (November), for the treatment of hepatitis B virus (HBV). It was also approved for use in Europe in 2008 (April) as a medication to treat hepatitis B virus (HBV) Teno-DF is a precursor drug prepared by providing a substituent of isopropylcarbonyl methoxy group as a structure of the lipophilic component into tenofovir in order to enhance the bioavailability of the tenofovir (MP 267-280° C., MW 287.21).

Hence, the most crucial issue in the synthesis of the Teno-DF is to synthesize the anti-viral major component tenofovir with high purity at high yield.

The base material used to synthesize tenofovir is hydroxypropyl adenine (HPA, ((R)-9-[2-(hydroxyl)propyl]adenine, MW. 193.2). It is the major challenge to minimize the formation of byproducts and degradation products in the synthesis of tenofovir from HPA.

As for tenofovir (phosphonomethoxypropyladenine, (R)-9-[2-(phosphonomethoxy)propyl]adenine, PMPA), the yield and purity of the final product tenofovir depends on the catalyzed chemical reaction of the ester product DEPMPA ((R)-9-[2-(diethylphosphonomethoxy)propyl]adenine) formed in the methylation of phosphate that is one of the steps in the synthesis of tenofovir from HPA. But, severe difficulties are encountered in the process of synthesizing DEPMPA from HPA at high yield and hydrolyzing DEPMPA into tenofovir (PMPA) with high purity and many researches have been made on this issue to continuously develop excellent synthesis methods and produce papers and patents on this matter.

The catalyzed chemical reaction uses a combination of different alkali catalyst and involves different organic solvents and extraction methods according to the individual reactions.

A condensation reaction between diethyl-p-toluenesulfonyloxymethylphosphonate (DEPTSMP) that is a substance to introduce methylene phosphate molecules and HPA is activated in the presence of an alkoxide catalyst used as a condensation catalyst, starting from lithium butoxide to magnesium butoxide, magnesium isopropoxide, a composite catalyst of sodium amide and magnesium acetate, or butyl magnesium chloride. After the production of tenofovir with high purity at high yield using the catalyst, the formation of the precursor derivative Teno-DF through the subsequent reaction can occur according to the conventional method.

But, the high content of impurities in the tenofovir product may have an adverse effect on the reactions of the subsequent step for synthesizing Teno-DF to lower the stability of the products using the Teno-DF and produce a large amount of degradation products exceeding the acceptable level, remaining highly deliquescent substances difficult to filter out in the step of separation of residues formed as byproducts in the reaction step and thus causing a considerable difficulty in commercialization based on Teno-DF. This eventually raises the cost of the materials.

It is reported that tenofovir disoproxil (Teno-D, MP 61-65° C., MW 519.45) with low purity causes formation of degradation products during its storage to produce Teno-D dimer that serves as a polymer itself (Organic Process Research & Development. 2010, Vol. 14, 1194-1201, Pharmaceutical Research, 2001, Vol. 18, 234-237).

PRIOR PATENT DOCUMENTS

[0008-1]
Laid-Open Patent CN 102219805A (Mar. 10, 2011)
Novel production process of tenofovir This patent discloses a method of using various catalysts to condensate HPA into methylene phosphate to produce diethylester, hydrolyzing the diethylester, and neutralizing a strong acid substance with 40% sodium hydroxide to pH 3 to obtain tenofovir crystals. This method inevitably uses a solution of 40% sodium hydroxide as a concentrated alkali neutralizing solution in consideration of the solubility of tenofovir, so it is difficult to obtain tenofovir that is a substance having a precise isoelectric point.

[0008-2]

Laid-Open Patent CN 102295660A (Jul. 4, 2011)

Process for synthesizing tenofovir

This patent describes a method of preparing ethylphosphate ester from HPA, hydrolyzing with hydrobromic acid, and neutralizing with a solution of sodium hydroxide to around pH 3.2 to obtain a precipitate.

[0008-3]

Laid-Open Patent CN 103374039A (Apr. 20, 2012)

Synthesis of tenofovir

This patent relates to a method of performing the same procedures of the patent in 0008-2 to hydrolyze and neutralize to pH 2.5-4.

[0008-4]

Laid-Open Patent CN 102899367B (Sep. 24, 2012)

A biological method and chemically combined with the method of synthetic tenofovir This patent discloses a method of using a carbonate as a neutralizing alkali solution to neutralize to pH 3.0.

[0008-5]

Laid-Open Patent CN 01239189B (Mar. 17, 2008)

Tenofovir, adefovir and intelligent polymer conjugates and preparation and use thereof This patent discloses a method of using a phosphate buffer solution to neutralize to pH 2-3.

[0008-6]

Laid-Open Patent US 2013/0165413 A1 (Jun. 27, 2013)

This patent is directed to a method of performing hydrolysis in the presence of various metal alkoxide catalysts as an alkali condensation catalyst, which includes various catalysts such as a composite catalyst of sodium amide and magnesium chloride, performing concentration at reduced pressure to concentrate the reactant solution to high concentration and then neutralizing with an aqueous alkali solution to pH 2-3. It also suggests the X-ray powder diffraction pattern (XRPD) of Teno-DF.

[0008-7]

US 2014/0303368 A1 (Oct. 9, 2014)

"Process for preparation of tenofovir"

This patent is similar to the patent 0008-6 and describes a method of synthesizing diethyltenofovir in the presence of a composite catalyst of aluminum and amide acid, performing a hydrolysis and then neutralizing with an aqueous alkali solution to pH 2-3.

NON-PATENT PAPERS (DOCUMENTS)

[0008-8]

Tetrahedron Letters 39 (1998) 1853-1856

"Practical synthesis of anti-HIV drug, PMP (PMPA, (R)-9-[2-(phosphonomethoxy)propyl]adenine)"

This paper specifies a method of using sodium hydride (NaH) or lithium tertiary butoxide as a catalyst to activate a methylene phosphate reaction of HPA into a diester compound, hydrolyzing the diester compound with a bromotrimethyl silane solution and then using a 50% aqueous solution of sodium hydroxide to neutralize to pH 3.

[0008-9]

Organic Process Research & Development (2010), Vol. 14, 1194p-1201

"Process improvements for manufacture of tenofovir disoproxil fumarate at commercial scale"

This document shows a method of using magnesium tertiary butoxide as a catalyst to prepare an ester from HPA through a methylene phosphate reaction, performing a hydrolysis to obtain tenofovir catalysts and then using a 40% aqueous solution of sodium hydroxide to neutralize to pH 2.8-3.2.

[0008-10]

Authorized USP Pending Monograph version 1 (2011)

"Tenofovir disoproxil fumarate"

The authorized USP pending monograph standards of this document places a limit on the content of ten or more impurities to standardize the purity of the raw materials. It can be seen from this document that a technical protection is set with precise technical power by the original development company (Gilead, USA) so that other companies should be disabled to synthesize tenofovir with ease (The expiration date of the Gilead patent is 2017, but the term of patent extends to 2018 if its extension is allowed according to the compensation of patent duration for extermination delay).

[0008-11]

World Health organization, Final Text for Addition to the International Pharmacopoeia (June, 2010)

"Tenofovir disoproxil fumarate"

The contents of this document were tentatively determined as the WHO international raw material standards.

The above eleven patents and documents show that the tenofovir products are obtained at low yield due to lots of impurities formed in the synthesis of tenofovir.

Therefore, the present invention relates to a novel synthesis method to realize high purity and high yield of the final product in the synthesis of tenofovir as a solution to the problems with the above-listed patents and documents.

DISCLOSURE OF INVENTION

Figure 1:
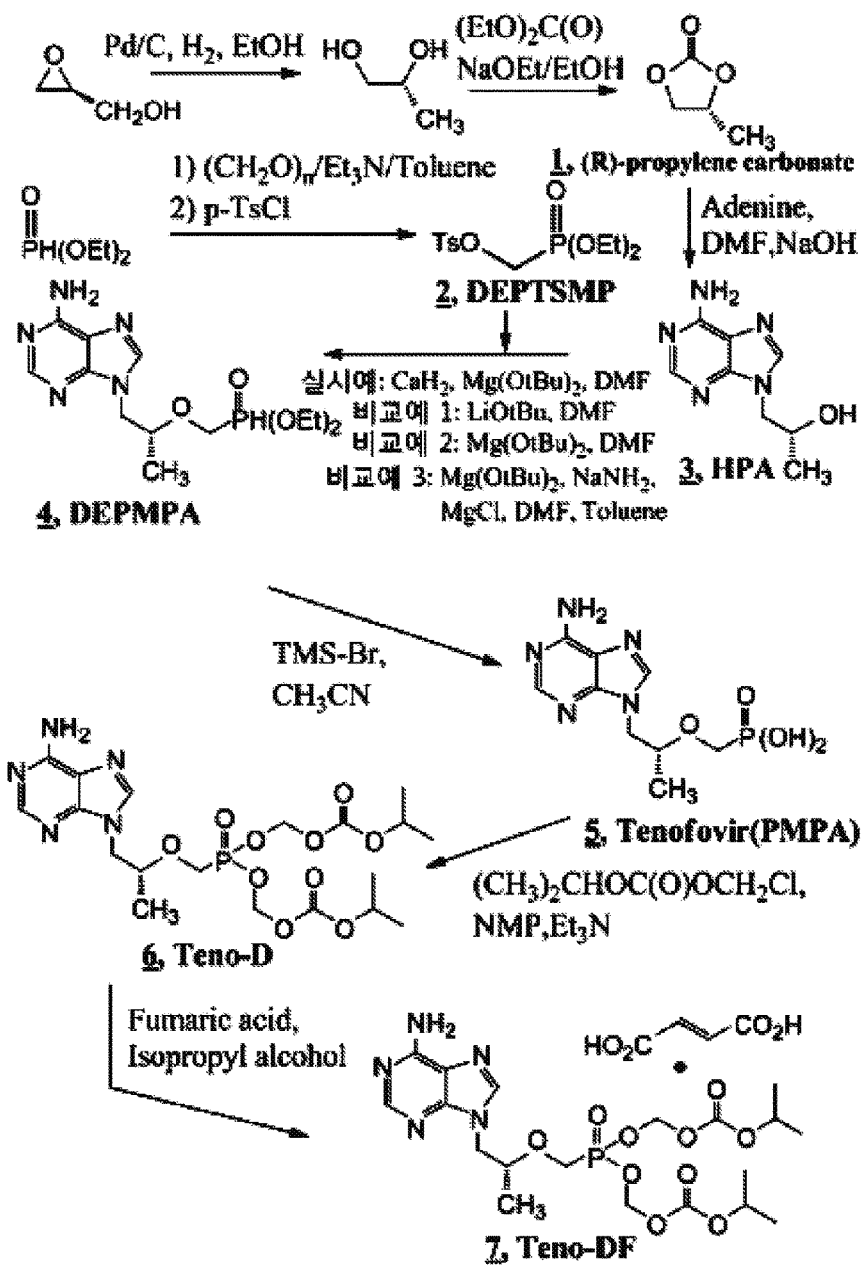
FIG. 1 is a process flow diagram depicting a synthesis mechanism and process flow of tenofovir disoproxil fumarate (hereinafter, referred to as "Teno-DF").
Figure 2:
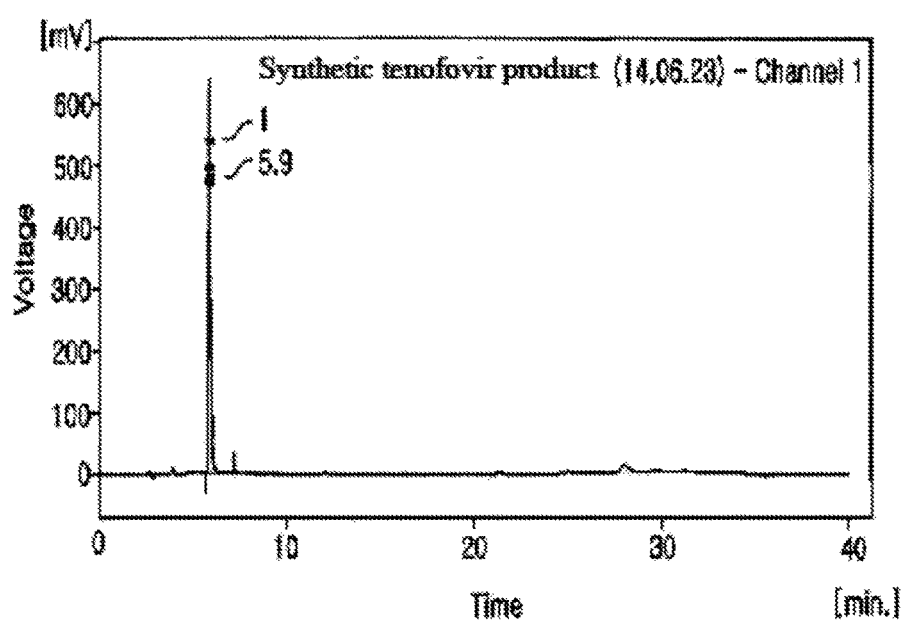
FIG. 2 is a graphical plot that illustrates a time response of a synthetic tenofovir product.
Figure 3:
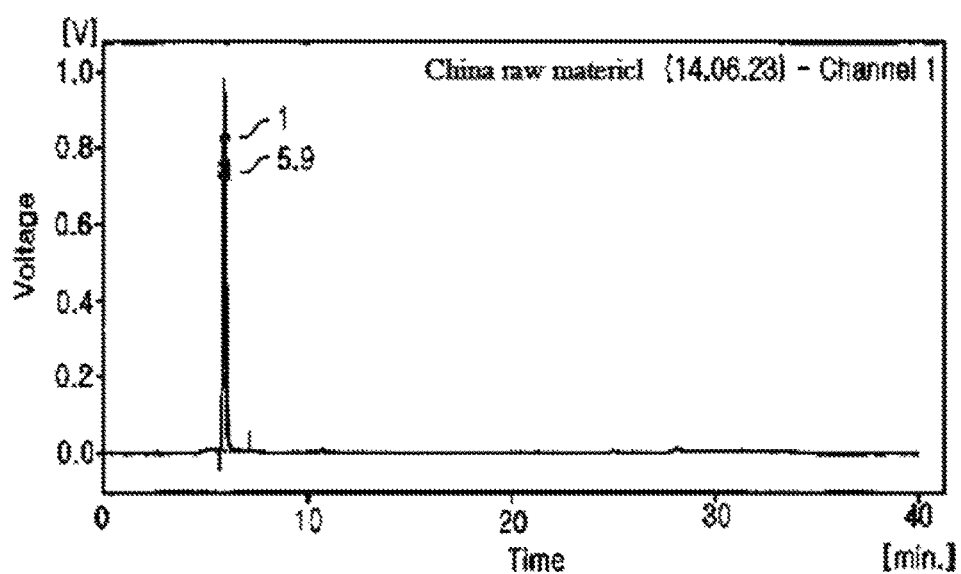
FIG. 3 is a graphical plot that illustrates a time response of a standard tenofovir product.
Figure 4:
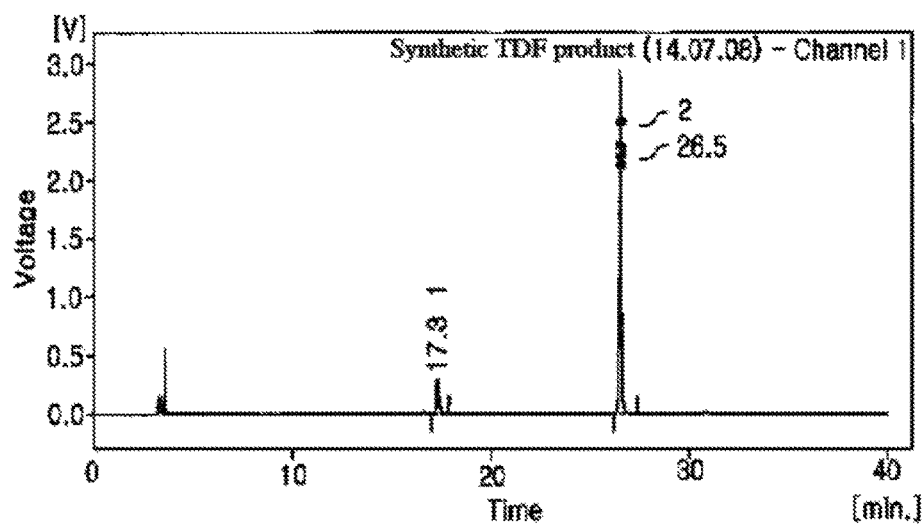
FIG. 4 is a graphical plot that illustrates a time response of a synthetic Teno-DF product.
Figure 5:
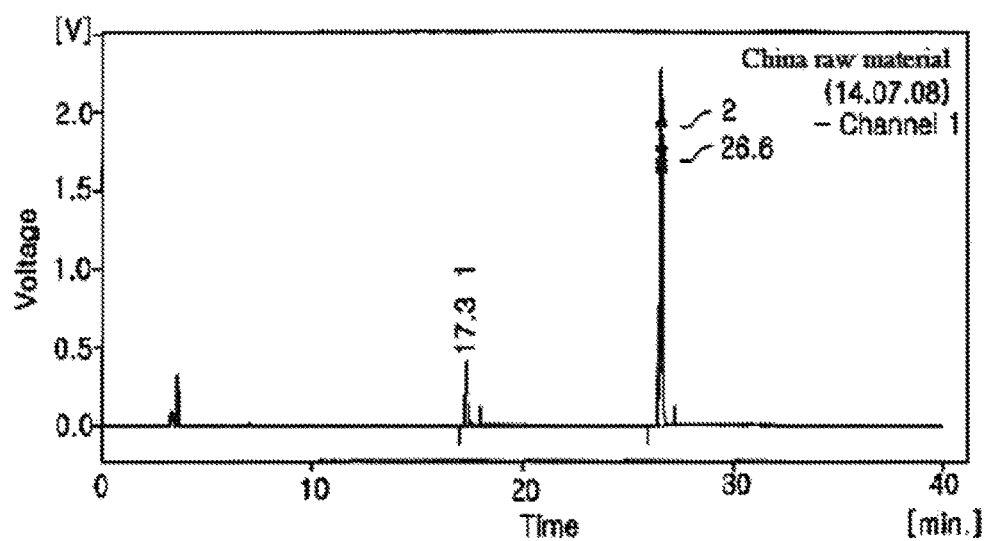
FIG. 5 is a graphical plot that illustrates a time response of a standard Teno-DF product.
Figure 6:
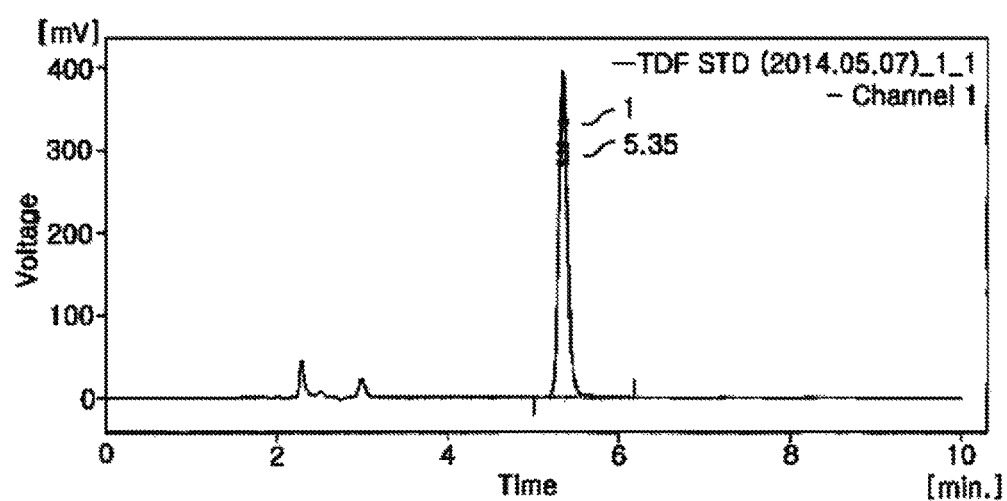
FIG. 6 is a graphical plot that illustrates a time response of a content test associated with a standard tenofovir DF product.
Figure 7:
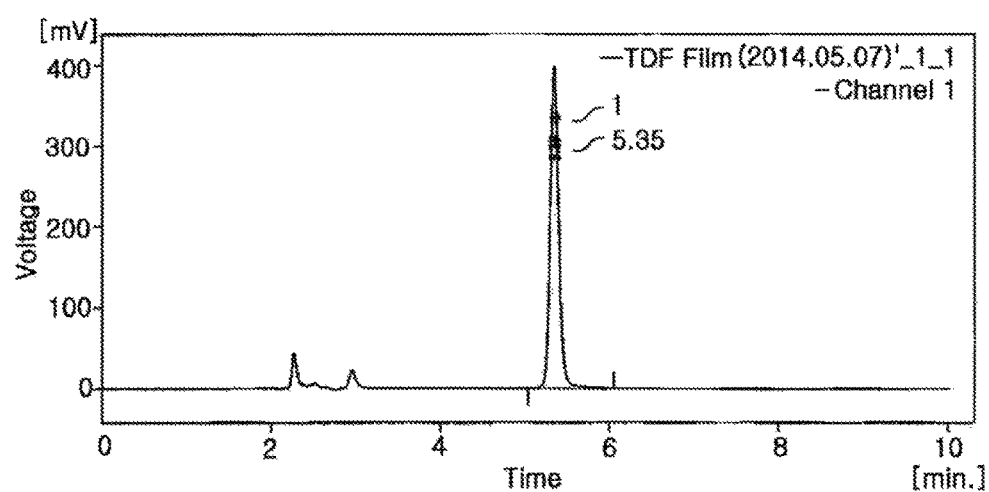
FIG. 7 is a graphical plot that illustrates a time response of a content test associated with a Teno-DF film.
Figure 8:
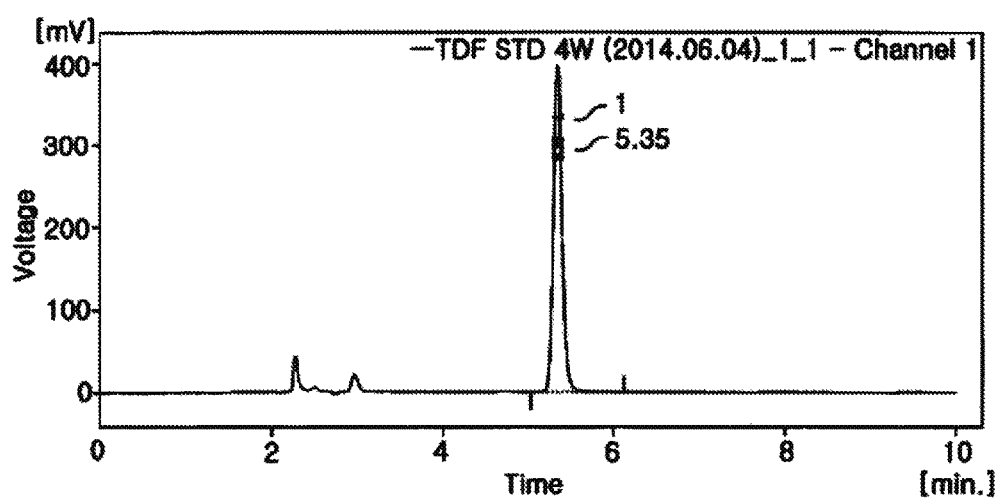
FIG. 8 is a graphical plot that illustrates a 4-week stability test for a standard Teno-DF product.
Figure 9:
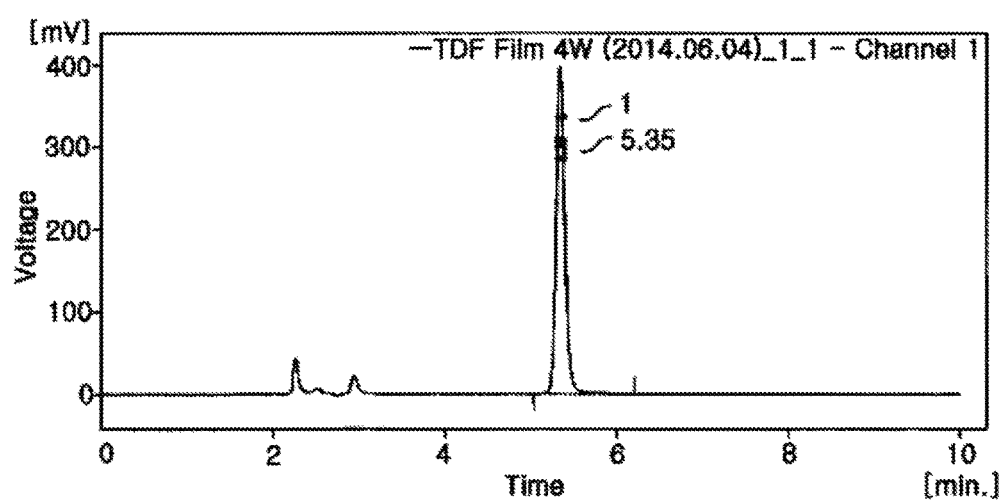
FIG. 9 is a graphical plot that illustrates a 4-week stability test for a Teno-DF film.
Figure 10:
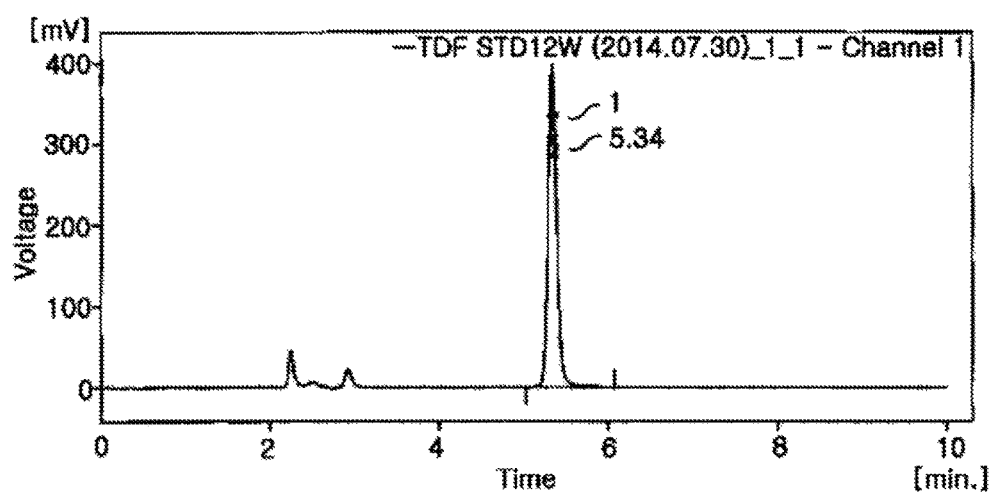
FIG. 10 is a graphical plot that illustrates a 12-week stability test for a standard Teno-DF product.
Figure 11:
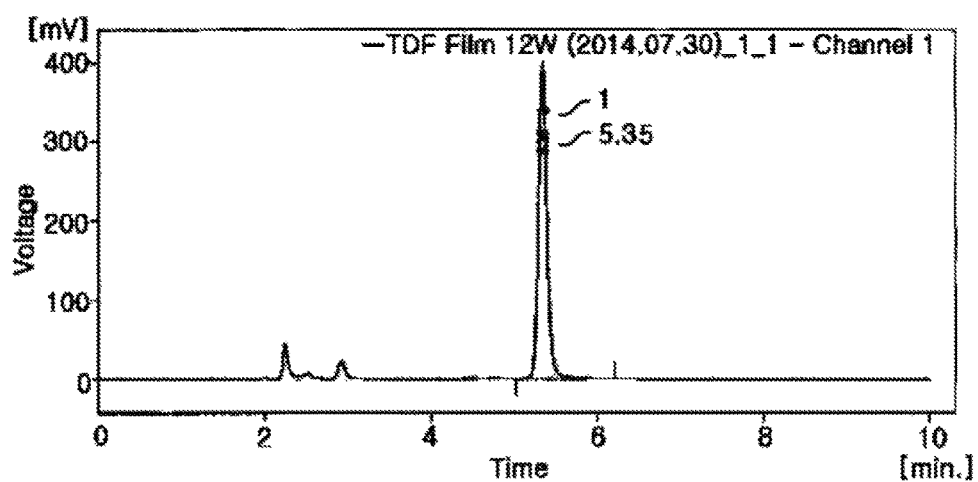
FIG. 11 is a graphical plot that illustrates a 12-week stability test for a Teno-DF film.
Figure 12:
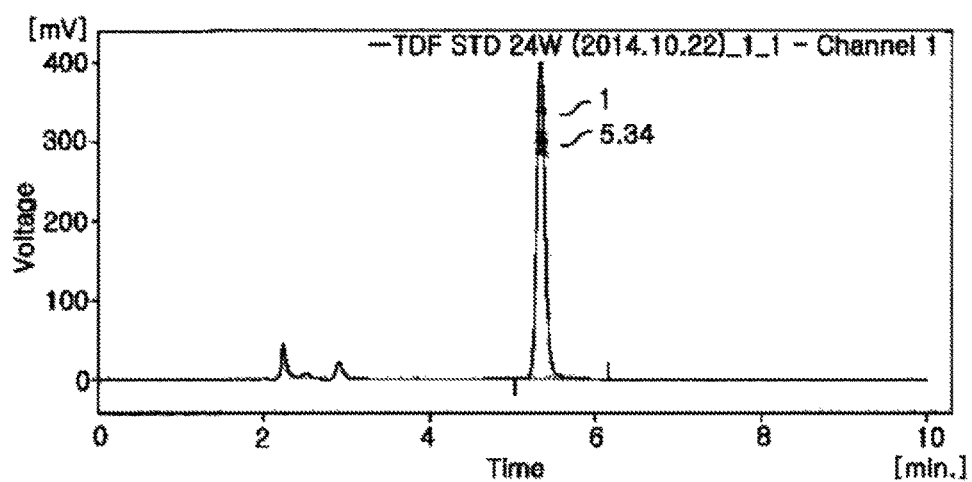
FIG. 12 is a graphical plot that illustrates a 24-week stability test for a standard Teno-DF product.
Figure 13:
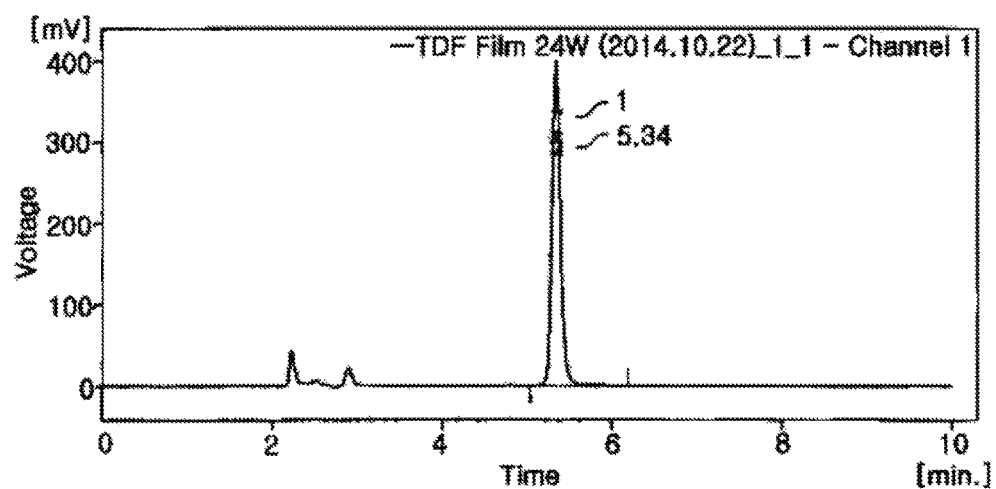
FIG. 13 is a graphical plot that illustrates a 24-week stability test for a Teno-DF film.

As for Viread® tablets that is a medication developed by Gilead Sciences Inc. (U.S.A.) and used to treat hepatitis B, its principal ingredient has a general name of tenofovir disoproxil fumarate; its melting point (MP) is 219° C., its MP is 635.52, and its chemical name according to the structural formula is 9-[2-(R)-[[bis[[(isopropoxycarbonyl)oxy]methoxy]phosphinyl]methoxy]propyl]adenine fumarate.

The Teno-DF was approved by the U.S. FDA in 2001, for the treatment of HIV, and in 2008 (November), for the treatment of hepatitis B virus (HBV). It was also approved for use in Europe in 2008 (April) as a medication to treat hepatitis B virus (HBV) Teno-DF is a precursor drug prepared by providing a substituent of isopropylcarbonyl methoxy group as a structure of the lipophilic component into tenofovir in order to enhance the bioavailability of the tenofovir (MP 267-280° C., MW 287.21). Therefore, the most crucial issue in the synthesis of the Teno-DF is to synthesize the anti-viral major component tenofovir with high purity at high yield. In the conventional technique for synthesis of tenofovir, an alkaline substance is used to control the pH value in the neutralization process, producing a lot of byproducts and degradation products in the course of crystallization of the tenofovir to increase the contamination of the tenofovir and thus to deteriorate the stability of the drug using tenofovir in the preparation of the drug.

Accordingly, the present invention is to provide a method for synthesizing tenofovir with high purity at high yield by minimizing the formation of byproducts and degradation products during the synthesis of tenofovir, which is the problem with the prior art, and to provide a method of preparing a drug using tenofovir in the form of film as a drug dosage form in order to enhance the bioactivity of the drug.

The present invention is directed to a method of determining a rapid reaction using a catalyst and reaction conditions to minimize the formation of byproducts and degradation products in the synthesis of tenofovir disoproxil fumarate and estimating the progress of the reaction during the synthesis process in a simple and precise manner. The present invention is also directed to a method of using an ion-exchange resin (Dowex 50W×4 hydrogen form, sulfonic acidic cation exchange resin) in the purification of an intermediate to yield the final product tenofovir with high purity and preparing an immediate release oral dissolving film using the tenofovir with high bioactivity.

Effects of the Invention

Unlike the prior art, the present invention uses an ion-exchange resin in combination with an alkaline compound used as a neutralizing agent in the preparation of tenofovir to precisely neutralize the synthesis solution and treats the solution with an organic solvent to enable the application of a simple low-pressure drying process at relatively low temperature. Accordingly, the present invention can not only synthesize tenofovir disoproxil fumarate with high purity while minimizing the formation of byproducts and degradation products, but also secure high stability of the final product relative to the conventional preparation methods.

BEST MODES FOR CARRYING OUT THE INVENTION

The present invention relates to a method for producing a raw material with higher purity than the allegedly improved prior art in the synthesis of tenofovir. Particularly, the present invention relates to a method of solving the problems like the isomeration of the reactants and the formation of highly deliquescent substances occurring in the course of the long-term synthesis process and preventing the production of molecular polymers during the synthesis process to synthesize a raw material with high purity.

The main mechanism of tenofovir synthesis generally involves reacting (R)-9-[2-(hydroxyl)propyl]adenine (HPA) and diethylparatolurene sulfonyloxymethyl phosphate (DEPTSMP) in the presence of a catalyst to yield a diethyl tenofovir ester compound (DEPMPA) and then hydrolyzing the DEPMPA to produce tenofovir (PMPA), which is an anti-viral substance. The subsequent synthesis of Teno-D and Teno-DF is just to convert the tenofovir to a precursor that is a fat-soluble substance made biologically active.

As described in the above-listed patents, the patents on the world-class developed techniques count on the improvement of the product yield and purity.

The present invention also relates to a method of adding a defined proportion of calcium hydride to magnesium butoxide that is a catalyst commonly used in the synthesis of DEPMPA from HPA to shorten the reaction time from 18 hours to 6 hours or less and cause the production of toluene calcium sulfonate to reduce highly deliquescent substances, and using an ion-exchange resin (Dowex 50W, sulfonic acid cation exchange resin) after neutralization with a counter-alkali solution in the dealcoholizing hydrolysis of the ester compound into tenofovir, thereby to reach a precise isoelectric point (pH 3.2) and further increase the synthesis yield of tenofovir. Generally, when the pH value is 2.5 to 3.5 in the neutralization, tenofovir ($H_2O$, one-molecule crystal water) is dissolved in the aqueous solution at about 7 percent. When the neutralization is perfectly performed with the ion-exchange resin, the solubility of tenofovir can be reduced to 4 percent or below.

The prior documents need to use the HPLC method that takes long time in order to estimate the progress of the reaction during the reaction process. But, the present invention just adds the TLC method to predict the results of the HPLC in advance.

Different reagents may be used in the hydrolysis process, but the present invention uses a selection of reagents that decrease the production of byproducts, desirably an alkyl-salicyl bromide reagent that works fast and reduces the reaction time.

As for the reaction time and temperature, the methyl phosphate esterification is activated at 75 to 80° C. for 4 to 6 hours, the hydrolysis at 80 to 90° C. for 4 to 6 hours, the tenofovir crystallization at 0 to 5° C. in the early-stage reaction.

<Estimation of the Progress of the Synthesis Reaction from HPA into Diethyl Tenofovir>
(a) TLC analysis conditions (UV 254 nm)
Developing solvent: methylene chloride (MC)/ethyl alcohol
(EtOH)=10/2,
Silica gel 60 F254,
25 Aluminum sheets 20×20 $cm^2$,
RF (HPA)=0.3,
RF (diethyl tenofovir)=0.4
(b) HPLC analysis conditions
USP Pending Monograph tenofovir disoproxil fumarate (2011),
UV detector 260 nm,
Column 4.6-mm 25 cm; 5 micro packing L1, Col. Temp. 35° C., Sam. Temp. 4° C. flow rate 1 ml/min. Inj. Sz. 10 micro L.
<Hydrolysis of Diethyl Tenofovir>
(a) TLC analysis conditions (UV 254 nm)
Developing solvent: methyl alcohol alone (100% MtOH), Silica gel 60 F254,
25 Aluminum sheets,
RF (tenofovir)=0.62,
Unreacted tenofovir ester is observed with MC/EtOH=10/2.

(b) HPLC analysis conditions

The conditions are all the same as in the estimation of the progress of the HPA reaction (the same as the USP Pending M. data).

<Estimation of the Progress of the Synthesis Reaction from Tenofovir into Tenofovir Disoproxil (Teno-D)>

(a) TLC analysis conditions (UV 254 nm)
Developing solvent: methyl alcohol alone,
Silica gel 60 F254,
Aluminum sheets,
RF (Teno-D)=0.75,
RF (tenofovir)=0.62

(b) HPLC analysis conditions

The conditions are all the same as in the estimation of the progress of the HPA reaction (the same as the USP Pending M. data).

COMPARATIVE EXAMPLES

Comparative Example 1

(a) Preparation Method of (R)-9-(2-hydroxypropyl) adenine (HPA)

40 g (0.296 mol) of adenine was dissolved in 200 ml of dimethylformamide (DMF), and 0.94 (0.0235 mol, 0.08 eq.) of sodium hydroxide (NaOH) was added. After 20-min agitation at the room temperature, 39.2 g (0.390 mol, 1.32 eq.) of (R)-propylene carbonate was added and the resultant solution was stirred for 30 minutes.

The reaction temperature was elevated to 120° C., and a thermal condensation reaction was activated for 24 hours. Subsequently, the reaction status was examined through TLC and HPLC. After the completion of the reaction (90% or above), the reaction temperature was reduced to 70° C. and 240 ml of isopropyl alcohol (IPA) was added to active crystallization. Under continuous agitation and cooling, crystals were collected through filtration at 10° C., washed with IPA and then dried out at 70° C. in a low-pressure dryer to obtain 41 g of HPA (yield 71.8%).

(b) Synthesis of Tenofovir ((R)-9-[2-(phosphonomethoxy)propyl]adenine)—Using Lithium Tertiary Butoxide Catalyst (Ref: Tetrahedron Letters 39 (1998) 1853)

40 g (0.21 mol) of HPA was dissolved in 200 ml of dimethylformamide (DMF), and 25.2 g (0.315 mol, 1.5 eq.) of lithium t-butoxide was added to make a suspension. At the reaction temperature of 30 to 35° C., 100 g (0.325 mol., 1.5 eq.) of diethyl-p-toluene suofonyloxymethyl phosphonate (DEPTSMP) was added repeatedly in two portions. With 5 or more hours of agitation at 80° C., the progress of the reaction was estimated through TLC and HPLC (taking 12 hours).

After the completion of the reaction, the resultant solution was cooled down to 20° C. and glacial acetic acid was added to adjust the pH value to 6-6.5 (weak acid). 1,000 ml of ethylacetate was added, and the resultant solution was heated up to 50 to 60° C., cooled down to 40° C. and subjected to filtration. 500 ml of ethylacetate was added to the byproduct, lithium inorganic residue, which was agitated, separated through filtration at the same time, combined with an organic solvent and washed twice with 100 ml of cold purified water at 10° C. or below and then with 50 ml of a saturated solution of sodium chloride. The organic layer was dehydrated with anhydrous sodium sulfate and separated under reduced pressure to obtain tenofovir ester (DEPMPA). 300 ml of toluene was added to the residue (DEPMPA), which was then distilled under reduced pressure to remove DMF and ethylacetate contained as impurities. 300 ml of cyclohexane was added to the residue and distillation under reduced pressure was performed to eliminate ethylacetate and DMF again. The DEPMPA was then subjected to a dealkylation reaction, that is, hydrolysis.

The tenofovir ester (DEPMPA) thus obtained was dissolved in 200 ml of acetonitrile and refluxed with 120 ml of bromotrimethylsilane. In five hours of the reaction, the reaction process was examined by way of TLC and HPLC and terminated (taking 14 hours). 200 ml of cold purified water was carefully added to dilute the resultant solution, and 200 ml of ethylacetate was used to wash the solution twice and remove the trimethylsilane component. Then, the resultant aqueous solution was concentrated under reduced pressure at the room temperature to separate the remaining amount of the solvent in the container and cooled down to 5° C.

The aqueous solution was neutralized with 50% sodium hydroxide and adjusted to pH 3. The crystals thus obtained were collected through filtration and washed with cold purified water (5° C.) to obtain tenofovir one-molecule crystal water ($H_2O$). The crystals were dried at 65° C. under reduced pressure (30 Torr) to obtain 35.2 g of crystals (yield 55.6%). The crystals thus obtained were dried at 100° C. under reduced pressure (30 Torr) again to yield 33 g of the final tenofovir crystals (anhydrous yield 55.4%). The anhydrous tenofovir was used to synthesize tenofovir disoproxil (Teno-D) and tenofovir disoproxil fumarate (Teno-DF) according to the methods disclosed in the prior documents.

Comparative Example 2

Synthesis of Tenofovir (Method of Using a Magnesium t-Butoxide Catalyst (Ref: Laid-Open Patent US2009/0286981 A1))

40 g (0.21 mol) of hydroxypropyl adenine (HPA) was dissolved in 80 ml of dimethylformamide (DMF), and 28.4 g (0.167 mol, 0.79 eq.) of magnesium t-butoxide was added to make a suspension. While the reaction temperature was maintained at 74° C., 80 g (0.2486 mol., 1.18 eq.) of diethyl-p-toluene suofonyloxymethyl phosphonate (DEPTSMP) was added dropwise for 21 hours. With 5 hours of agitation at 80° C., the progress of the reaction was estimated through TLC and HPLC (taking 26 hours).

After the completion of the reaction, the resultant solution was cooled down to 20° C. and 24 g (0.4 mol) of glacial acetic acid was added to adjust the pH value to 6-6.5 (weak acid). The reactant solution was then completely distilled under reduced pressure at 80° C. The residual reactant solution was cooled down to 20° C., and 240 ml of methylene chloride and 40 ml of purified water were added to prepare an inorganic substance, which was filtered out to separate an organic layer. The aqueous layer and the inorganic residue were subjected to additional extraction with 100 ml of MC and filtration to eliminate the inorganic residue. After addition of an organic solvent, 50 ml of cold purified water (10° C. or below) and then 50 ml of a saturated solution of sodium chloride were sequentially used to wash the organic layer. The organic layer was dehydrated with anhydrous sodium sulfate and then distilled under reduced pressure to yield tenofovir ester (DEPMPA). 200 ml of toluene was added to the residue, and distillation was performed under reduced pressure to eliminate the remaining DMF. The residual solution, DEPMPA was then subjected to a dealkylation reaction, that is, hydrolysis.

260 ml of an aqueous solution of HBr was added to the tenofovir ester (DEPMPA), and the resultant solution was stirred at 90° C. for 5 hours. In 5 hours of the reaction, the reaction process was examined through TLC and HPLC and terminated (taking 10 hours). 120 ml of cold purified water was carefully added to dilute the reactant solution, and 120 ml of MC was used to wash the reactant solution twice and eliminate the trimethylsilane component. The aqueous solution thus obtained was concentrated under slightly reduced pressure at the room temperature to eliminate the remaining MC in the container and cooled down to 5° C.

Once cooled down, the aqueous solution was neutralized with a 40% solution of sodium hydroxide to pH 2.5-3.0. The crystals thus obtained were collected through filtration and washed with cold purified water (5° C.) to obtain tenofovir crystals. The crystals were dried at 65° C. under vacuum (30 Torr) to obtain 44 g of crystals (yield 70%). The crystals thus obtained were dried at 100° C. under reduced pressure (30 Torr) again to yield 41.2 g of tenofovir crystals (anhydrous yield 69%). The anhydrous tenofovir was used to synthesize tenofovir disoproxil (Teno-D) and tenofovir disoproxil fumarate (Teno-DF) according to the methods disclosed in the prior documents.

Comparative Example 3

Synthesis Method for Tenofovir
(Method of Using a Composite Catalyst of Sodium Amide and Magnesium Chloride (Ref: Laid-Open Patent US2013/0165413 A1))

40 g (0.21 mol) of hydroxypropyl adenine (HPA) was dissolved in 80 ml of dimethylformamide (DMF). While the reaction temperature was maintained at 0° C., 16.16 g of sodium amide was added and the resultant solution was agitated for 30 minutes. 19.7 g of magnesium chloride was then added at 25° C. After one-hour agitation, 120 ml of toluene was added, and 100 g (0.31 mol, 1.48 eq.) of diethyl-p-toluene suofonyloxymethyl phosphonate (DEPTSMP) was added dropwise at 75~80° C. for 4 hours. With 5 hours of agitation at 80° C., the progress of the reaction was estimated through TLC and HPLC (taking 16 hours).

After the completion of the reaction, the resultant solution was completely distilled under reduced pressure at 70° C. The residual reactant solution was cooled down to 20° C., and 240 ml of methylene chloride and 40 ml of purified water were added to prepare an inorganic substance, which was filtered out to separate an organic layer. The aqueous layer and the inorganic residue were subjected to additional extraction with 100 ml of MC and filtration at the same temperature, removing the inorganic residue. After addition of an organic solvent, 50 ml of cold purified water (10° C. or below) and then 50 ml of a saturated solution of sodium chloride were sequentially used to wash the organic layer. The organic layer was dehydrated with anhydrous sodium sulfate and then distilled under reduced pressure to yield tenofovir ester (DEPMPA). 100 ml of toluene was added to the residue, and distillation was performed under reduced pressure to eliminate the remaining DMF. The residual solution, DEPMPA was then subjected to a dealkylation reaction, that is, hydrolysis.

260 ml of an aqueous solution of HBr was added to the tenofovir ester (DEPMPA), and the resultant solution was stirred at 90° C. for 5 hours. In 5 hours of the reaction, the reaction process was examined through TLC and HPLC and terminated (taking 10 hours). 120 ml of cold purified water was carefully added to dilute the reactant solution, and 120 ml of MC was used to wash the reactant solution twice and eliminate the trimethylsilane component. The aqueous solution thus obtained was concentrated under slightly reduced pressure at the room temperature to eliminate the remaining MC in the container and cooled down to 5° C.

Subsequently, the aqueous solution was neutralized with a 50% solution of sodium hydroxide to pH 2.5-3.0. The crystals thus obtained were collected through filtration and washed with cold purified water (5° C.) and again with 40 ml of cold acetone to obtain tenofovir one-molecule crystal water ($H_2O$). 360 ml of purified water was added to the crystals, which was then heated up to 90° C. for 30 minutes, cooled down to 0° C. and, in four hours, subjected to filtration. The crystals were dried at the internal temperature of 65° C. in a drier under vacuum (30 Torr) to obtain 36 g of crystals (yield 57%). The crystals thus obtained were dried at 100° C. under reduced pressure (30 Torr) again to yield 33.7 g of anhydrous tenofovir crystals (anhydrous yield 56.6%).

The anhydrous tenofovir was used to synthesize tenofovir disoproxil (Teno-D) and tenofovir disoproxil fumarate (Teno-DF) according to the methods disclosed in the prior documents.

EXAMPLE

Synthesis Method for Tenofovir (Novel Method)
(Method of Using a Composite Catalyst of Magnesium t-Butoxide and Calcium Hydride and an Ion-Exchange Resin)

40 g (0.21 mol) of (R)-9-(2-hydroxypropyl)adenine (HPA) was dissolved in 200 ml of dimethylformamide (DMF), and 143.2 g (0.84 mol, 4.0 eq.) of magnesium t-butoxide and 4.42 g (0.105 mol) of calcium hydride as a catalyst were added to make a suspension. While the reaction temperature was maintained at 30 to 35° C., 100 g (0.325 mol, 1.5 eq.) of diethyl-p-toluene sulfonyloxymethyl phosphonate (DEPTSMP) was added dropwise for 2 hours. With 5 or more hours of agitation at 80° C., the progress of the reaction was estimated through TLC and HPLC (taking 7 hours).

After the completion of the reaction, acetic acid was added dropwise at 20° C. to control the pH value between 6 and 6.5. 1,000 ml of ethyl acetate was added to the reactant solution, which was then heated up to 50 to 60° C., cooled down to 40° C. and subjected to filtration. The inorganic residue was additionally extracted cation with 500 ml of ethyl acetate and filtered at the same temperature, removing inorganic substances. After addition of an organic solvent, the solvent was separated under reduced pressure at 70° C. or below. The residual solution thus obtained was cooled down to 20° C. or below and subjected to separation using 1,000 ml of ethyl acetate and 100 ml of cold purified water. The organic layer separated was washed twice with 100 ml of cold water and then with 50 ml of a saturated saline solution (sodium chloride solution), dehydrated with anhydrous sodium sulfate, and separated under reduced pressure to obtain tenofovir ester (DEPMPA). 300 ml of toluene was added to the residue to eliminate the remaining DMF and ethyl acetate under reduce pressure. Subsequently, 300 ml of cyclohexane was added, and distillation was performed under reduced pressure to eliminate ethyl acetate and DMF. The residual solution, DEPMPA was then subjected to a dealkylation reaction, that is, hydrolysis.

The tenofovir ester (DEPMPA) was dissolved in 200 ml of acetonitrile and then refluxed with 120 ml of bromotrimethylsilane. In 5 hours of the reaction, the reaction process was examined through TLC and HPLC and terminated (taking 12 hours). 200 ml of cold purified water was carefully added to dilute the reactant solution, which was then washed twice with 200 ml of ethyl acetate to remove the trimethylsilane component. The aqueous solution thus obtained was concentrated under slightly reduced pressure at the room temperature to eliminate the remaining solvent in the container and cooled down to 5° C.

Subsequently, the aqueous solution was neutralized with a 40% solution of sodium hydroxide to pH 3.5, and a reverse ion-exchange resin (Dowex 50W cation exchange resin) was used to precisely control the pH value to 3.2. The crystals thus obtained were collected through filtration and washed with cold purified water (5° C.) to obtain tenofovir crystals. The crystals were dissolved in 400 ml of methanol, filtered to remove the ion-exchange resin and concentrated under reduced pressure. The residual crystals were dried at the internal temperature of 65° C. in a drier under vacuum (30 Torr) to obtain 48.0 g of tenofovir crystals (yield 75.9%). The crystals thus obtained were dried at 95° C. under reduced pressure (30 Torr) again to yield 45 g of anhydrous tenofovir crystals (anhydrous yield 75.7%).

The anhydrous tenofovir was used to synthesize tenofovir disoproxil (Teno-D) according to the following procedures.

[Synthesis Method for Tenofovir Disoproxil (Teno-D)]

25 g of the anhydrous tenofovir obtained in the Example was added to 100 ml of n-methyl-2-pyrrolidinone (NMP) and 50 ml of toluene, and the resultant solution was distilled under reduced pressure at 60° C. and removed of water. 50 ml of toluene was further added and distillation was performed.

The reactant solution was cooled down to 35° C., and 35.2 g (4 eq.) of triethylamine was added to form crystals. Agitation was continued to make a homogeneous suspension. 28 g (1.0 eq.) of tetrabutylammonium bromide was added, and the resultant solution was heated up to 45° C.

66.4 g (5.0 eq.) of chloromethyl isopropyl carbonate was added to the solution, which was continuously stirred at 45.55° C. In 5 hours of the reaction, TLC and HPLC were used to estimate the progress of the reaction, and the reaction was terminated. As the sticky solution became clear and reddish, it was cooled down to the room temperature, mixed with 150 ml of cyclohexane, and vigorously stirred. The solution was removed of the supernatant using a low-pressure pipette and washed with 100 ml of cyclohexane. 300 ml of ethyl acetate and 100 ml of cold water were added to the reactant layer, which was then stirred and removed of the aqueous layer. The aqueous layer thus obtained was washed twice with 50 ml of ethyl acetate and combined with the crude solution. The organic layer was washed with 50 ml of cold water and 50 ml of saturated saline solution, dehydrated with magnesium sulfate and then isolated under reduced pressure to yield 53 g of tenofovir disoproxil in the form of crystalline sludge. The sludge was further cooled down to the lower temperature to form crystals and then subjected to quantitative analysis through HPLC (purity 85%, actual amount per area 45 g, yield 96%).

[Synthesis Method for Tenofovir Disoproxil Fumarate (Teno-DF]

53 g (actual 45 g)(0.087 mol) of tenofovir disoproxil coarse crystals were dissolved in 120 ml of isopropyl alcohol, and 12.5 g (0.107 mol, 1.2 eq.) of fumaric acid was added. The resultant solution was stirred at 50 to 55° C. for 2 hours and sufficiently cooled down to 3 to 5° C. to form crystals. After sufficient agitation, the crystals were filtered out and suspended with 250 ml of ethyl acetate. After one-hour agitation, the reactant solution was cooled down to 10° C. or below, filtered and washed. The crystals thus obtained were dried under vacuum at 40° C. to yield 35 g of tenofovir disoproxil fumarate (HPLC area purity 98.5%, yield 63.6%).

[Method of Manufacturing Film Dosage Form]

TABLE 1

| Composition | Example 1 | Example 2 | Example 3 |
|---|---|---|---|
| Teno-DF | 37.5% (150 mg of Teno-DF) | 37.5% (150 mg of Teno-DF) | 37.5% (150 mg of Teno-DF) |
| Hydroxypropyl methyl cellulose | — | 20.00% | 20.00% |
| Flurane | 35.0% | 15.00% | 15.00% |
| Polyethylene glycol 600 | 15% | 15% | — |
| Polyethylene glycol 400 | — | — | 15% |
| Glycerin | 2% | 2% | 2% |
| Polysorbate 20 | 0.10% | 0.10% | 0.10% |
| Acesulfame | 10.40% | 10.40% | 10.40% |
| Purified water | q.s | q.s. | q.s. |
| Subtotal | 100% | 100% | 100% |
| Total weight (mg/sheet) | 400 mg | 400 mg | 400 mg |

(Note:
The content of each ingredient indicates wt. % with respect to the total weight)

Example 1

1. Polyethylene glycol 600, glycerin, polysorbate 20, and acesulfame are completely dissolved in purified water.
2. Flurane is completely dissolved in the solution of the step 1 to prepare a mixed solution.
3. The mixed solution is aged at room temperature (25° C.) for 12 hours or longer.
4. The principal ingredient, tenofovir disoproxil fumarate is added to the mixed solution, and the resultant solution is vigorous stirred.
5. The mixed solution is applied so that 150 mg of the principal ingredient is contained in area of 12 cm$^2$.
6. After application, drying is performed at 65° C. for 30 minutes and at 45° C. for at least 3 hours.

Example 2

The procedures are performed in the same manner as described in the preparation method of Example 1, excepting that the flurane content is 15 wt. %, the hydroxypropyl methyl cellulose content 20 wt. %.

Example 3

The procedures are performed in the same manner as described in the preparation method of Example 2, excepting that polyethylene glycol 400 is used in the place of polyethylene glycol 600 at the content of 15 wt. %.

[Property Test and Analysis Methods and Evaluation for Film Dosage Form]

(1) Sensory Test
1=not bitter
2=slightly bitter
3=moderately bitter
4=very bitter
5=extremely bitter (2) Bending Test The bending test involves determining the frequency of folding a fast-dissolving film in half with two fingers as required to split the film in half. The test was carried out in 30 minutes after the fast-dissolving film is released. The temperature and humidity conditions were 22° C. and 55% RH, respectively. The higher frequency implicitly indicates the less brittleness.

(3) Disintegration Test

The test is performed using plates according to the Guidelines on Specification of Disintegration test for general release dosage form of Korean Pharmacopoeia (KP). In the testing, the disintegration time should be 3 minutes or less.

(4) Peel Test

The peel test is to measure how easy the test film is peeled out from a PET film used as a support film.
1=very hard to peel
2=hard to peel
3=moderately peeled
4=easy to peel
6=very easy to peel (5) Evaluation Table for Film Dosage Form

TABLE 2

|  | Example 1 | Example 2 | Example 3 |
|---|---|---|---|
| Sensory test | 3 | 3 | 3 |
| Bending test | 3 | 5 | 8 |
| Disintegration test | 3 minutes or less | 3 minutes or less | 3 minutes or less |
| Peel test | 5 | 5 | 5 |

Test and Analysis Methods and Evaluation
<HPLC Data: Comparative HPLC Data Between Tenofovir and Teno-DF>

[Improvement and Comparative Evaluation of Synthesis Method for Tenofovir and General Evaluation for Film Dosage Form]

The novel synthetic method (Example) produced 45 g of tenofovir (the weight of the final product, tenofovir crystals) from 40 g of the HPA raw material to achieve a yield of 1.125 ratio (yield 112.5%), which was higher than the yields of the Comparative Examples; 82.5% (33/40=0.825) for Comparative Example 1, 103% (41.2/40=1.03, the yield was increased by about 9.5%, theoretic yield increase=6.7% (69%→75.7%)) for Comparative Example 2, and 84.2% (33.7/40=0.842) for Comparative Example 3.

Moreover, the yield of the final tenofovir disoproxil fumarate (Teno-DF) produced from the tenofovir (anhydrous) synthesized by the synthesis method of the present invention via the intermediate step of tenofovir disoproxil (Teno-D) was 140% (1.4 portion), that is, producing 35 g of the Teno-DF product from 25 g of the tenofovir (anhydrous) raw material. The proportion based on the synthesis interval in the production step was similar to the synthesis yield ratio of 1.38 (138%, 69/50=1.38) shown in the non-patent document "Organic Process Research & Development (2010, Vol. 14, 1194-1201).

Accordingly, it can be seen that the synthesis method of the present invention capable of producing tenofovir with high yield is more excellent and effective than the conventional synthesis methods.

Furthermore, as the film dosage form of the medicine using the tenofovir disoproxil fumarate thus synthesized is proved stable, the medicinal products using the tenofovir disoproxil fumarate synthesized according to the present invention can be developed into a novel film type preparation.

What is claimed is:

1. A method for preparing tenofovir crystals, which method is to synthesize tenofovir and prepare tenofovir crystals using the synthesized tenofovir, the method comprising:
   (a) dissolving hydroxypropyl adenine (HPA) in dimethyl formamide (DMF);
   (b) adding magnesium butoxide and calcium hydride as a catalyst to the solution of the step (a) and making a suspension;
   (c) adding diethyltoluene sulfonyloxymethyl phosphate to the solution of the step (b) to activate a reaction;
   (d) after completion of the reaction, washing the solution of the step (c) with ethyl acetate and purified water, dehydrating an organic layer with anhydrous sodium sulfate and rendering the organic layer under reduced pressure to obtain tenofovir ester;
   (e) dissolving the tenofovir ester of the step (d) in acetonitrile and adding bromotrimethylsilane;
   (f) using a sulfonic acidic cation exchange resin to adjust the pH value of the solution of the step (e); and
   (g) washing, concentrating and drying the solution of the step (f) under reduced pressure to obtain anhydrous tenofovir crystals.

2. The method as claimed in claim 1, wherein the catalyst is added in an amount to use 300 to 400 parts by weight of magnesium butoxide and 3 to 11 parts by weight of calcium hydride with respect to 100 parts by weight of the raw material.

3. A method for preparing an oral dissolving film formulation of a medicine for treatment of a viral disease using tenofovir disoproxil fumarate as a component, the method comprising:
   (a) dissolving hydroxypropyl adenine (HPA) in dimethyl formamide (DMF);
   (b) adding magnesium butoxide and calcium hydride as a catalyst to the solution of the step (a) and making a suspension;
   (c) adding diethyltoluene sulfonyloxymethyl phosphate to the solution of the step (b) to activate a reaction;
   (d) after completion of the reaction, washing the solution of the step (c) with ethyl acetate and purified water, dehydrating an organic layer with anhydrous sodium sulfate and rendering the organic layer under reduced pressure to obtain tenofovir ester;
   (e) dissolving the tenofovir ester of the step (d) in acetonitrile and adding bromotrimethyl silane;
   (f) using a sulfonic acidic cation exchange resin to adjust the pH value of the solution of the step (e);
   (g) washing, concentrating and drying the solution of the step (f) under reduced pressure to obtain anhydrous tenofovir crystals;
   (h) mixing the tenofovir crystals obtained in the step (g) with N-methyl-2-pyrrolidinone and toluene, making vacuum distillation thereof, and heating after adding triethylamine and tetrabutylammonium bromide thereto;

(i) adding chloromethylisopropyl carbonate to the solution of the step (h), stirring them, and obtaining a tenofovir disoproxil crystal after washing and dehydration;
(j) dissolving the tenofovir disoproxil crystals obtained in the step (i) in isopropyl alcohol, adding fumaric acid and obtaining a crystal after stirring and cooling and filtering;
(k) suspending and stirring the crystals obtained in the step (j) in ethyl acetate;
(l) obtaining tenofovir disoproxil fumarate by filtering, washing and vacuum-drying the reaction solution produced in the step (k);
(m) obtaining a mixed solution by dissolving tenofovir disoproxil fumarate obtained in the step (l) and polyethylene glycol 600, glycerin, polysorbate 20 and acesulfame in a purified water;
(n) adding one or more stabilizers selected from hydroxypropyl methylcellulose and flurane in the mixed solution obtained in the step (m); and
(o) preparing a film formulation by applying and drying the mixture produced in the step (n).

* * * * *